United States Patent
Sato

(10) Patent No.: US 8,071,756 B2
(45) Date of Patent: *Dec. 6, 2011

(54) POLYSACCHARIDE PSEUDO-SPONGE

(75) Inventor: Tomoya Sato, Saitama-ken (JP)

(73) Assignee: Seikagaku Corporation, Tokyo (JP)

( * ) Notice: Subject to any disclaimer, the term of this patent is extended or adjusted under 35 U.S.C. 154(b) by 836 days.

This patent is subject to a terminal disclaimer.

(21) Appl. No.: 10/570,884

(22) PCT Filed: Sep. 10, 2004

(86) PCT No.: PCT/JP2004/013247
§ 371 (c)(1),
(2), (4) Date: Sep. 15, 2006

(87) PCT Pub. No.: WO2005/026214
PCT Pub. Date: Mar. 24, 2005

(65) Prior Publication Data
US 2007/0009579 A1    Jan. 11, 2007

(30) Foreign Application Priority Data
Sep. 12, 2003 (JP) .................... 2003-322181

(51) Int. Cl.
*C07H 5/04* (2006.01)
*C07H 5/06* (2006.01)
*C07H 3/00* (2006.01)

(52) U.S. Cl. ........ 536/53; 536/55.2; 536/55.3; 536/123; 536/123.12; 536/124

(58) Field of Classification Search ............ 536/53, 536/55.2, 55.3, 123, 123.12, 124
See application file for complete search history.

(56) References Cited

U.S. PATENT DOCUMENTS

| | | | |
|---|---|---|---|
| 5,462,976 A | 10/1995 | Matsuda et al. | |
| 5,763,504 A | 6/1998 | Matsuda et al. | |
| 5,789,462 A | 8/1998 | Motani et al. | |
| 6,025,444 A | 2/2000 | Waki et al. | |
| 6,031,017 A | 2/2000 | Waki et al. | |
| 6,107,410 A | 8/2000 | Waki et al. | |
| 6,425,918 B1 * | 7/2002 | Shapiro et al. ........ | 623/11.11 |
| 6,602,859 B2 | 8/2003 | Miyamoto et al. | |
| 2004/0076811 A1 | 4/2004 | Sato | |

FOREIGN PATENT DOCUMENTS

| | | |
|---|---|---|
| EP | 763754 A2 | 3/1997 |
| EP | 1369441 A1 | 12/2003 |
| JP | 8-301903 A | 11/1996 |
| JP | 9-136902 A | 5/1997 |
| JP | 11-192081 A | 7/1999 |
| JP | 11-319068 A | 11/1999 |
| WO | WO 02/060971 A1 | 8/2002 |

OTHER PUBLICATIONS

Sato, WO 2002/060971 A1, Derwent Abstract.*

* cited by examiner

*Primary Examiner* — Shaojia Anna Jiang
*Assistant Examiner* — Everett White
(74) *Attorney, Agent, or Firm* — Nixon & Vanderhye P.C.

(57) ABSTRACT

A photocrosslinked polysaccharide pseudo-sponge exhibiting a low swelling property and a high degradation ability in vivo while retaining a suitable strength. The polysaccharide pseudo-sponge is produced by a crosslinking reaction of a photoreactive polysaccharide obtained by introducing a photoroactive group into a polysaccharide, and exhibits a low swelling property and a blue dextran-low dyaffinity.

15 Claims, 9 Drawing Sheets

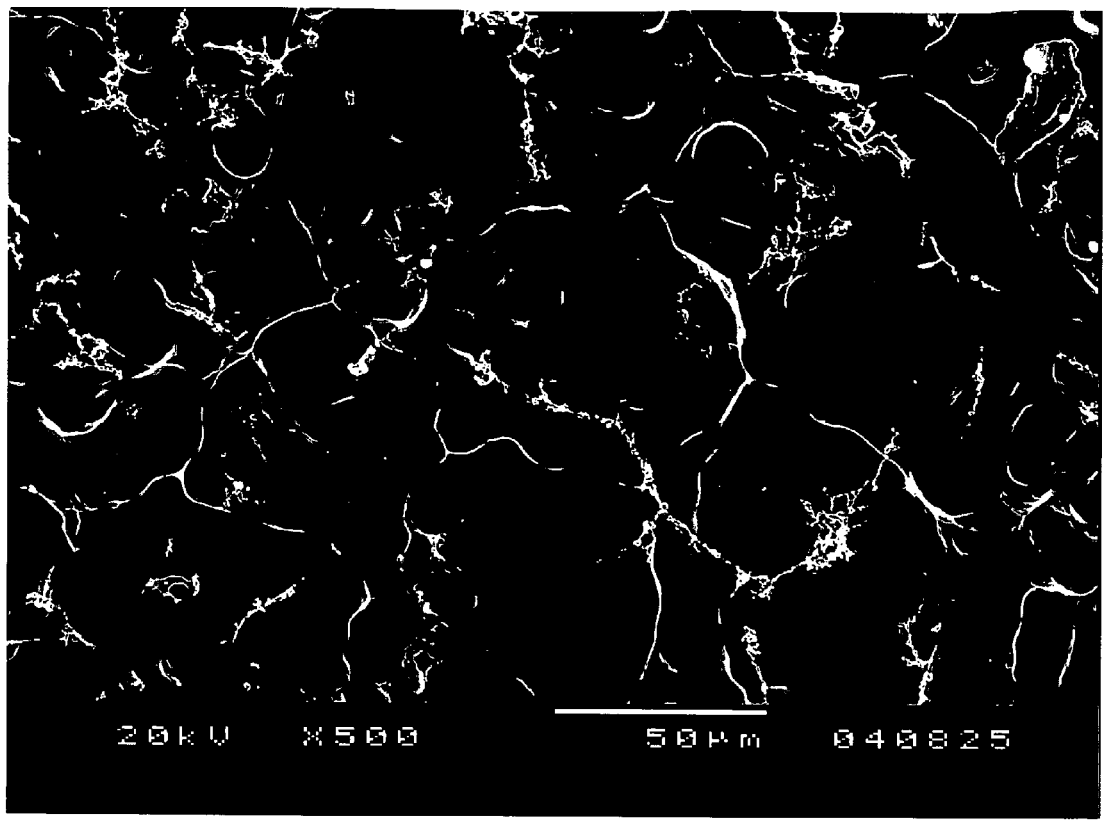
Fig. 6    an enlarged view of the surface of a polysaccharide pseudo-sponge 2

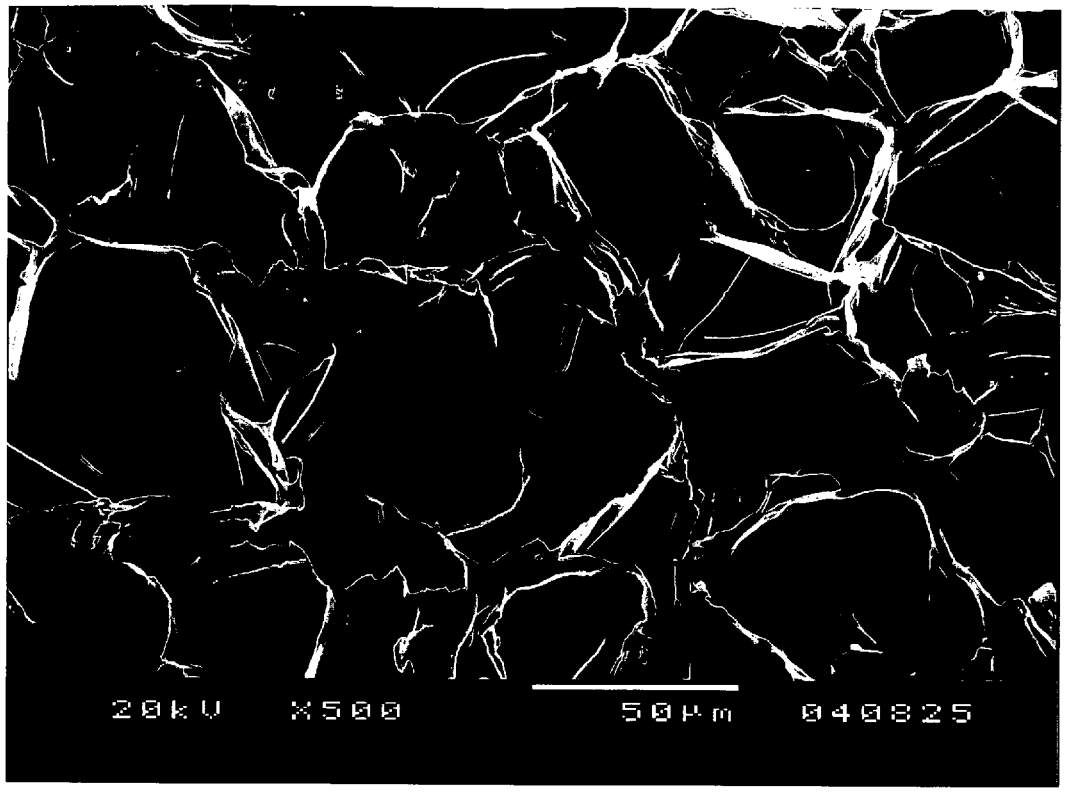
Fig. 7  an enlarged view of a section of a polysaccharide pseudo-sponge 2

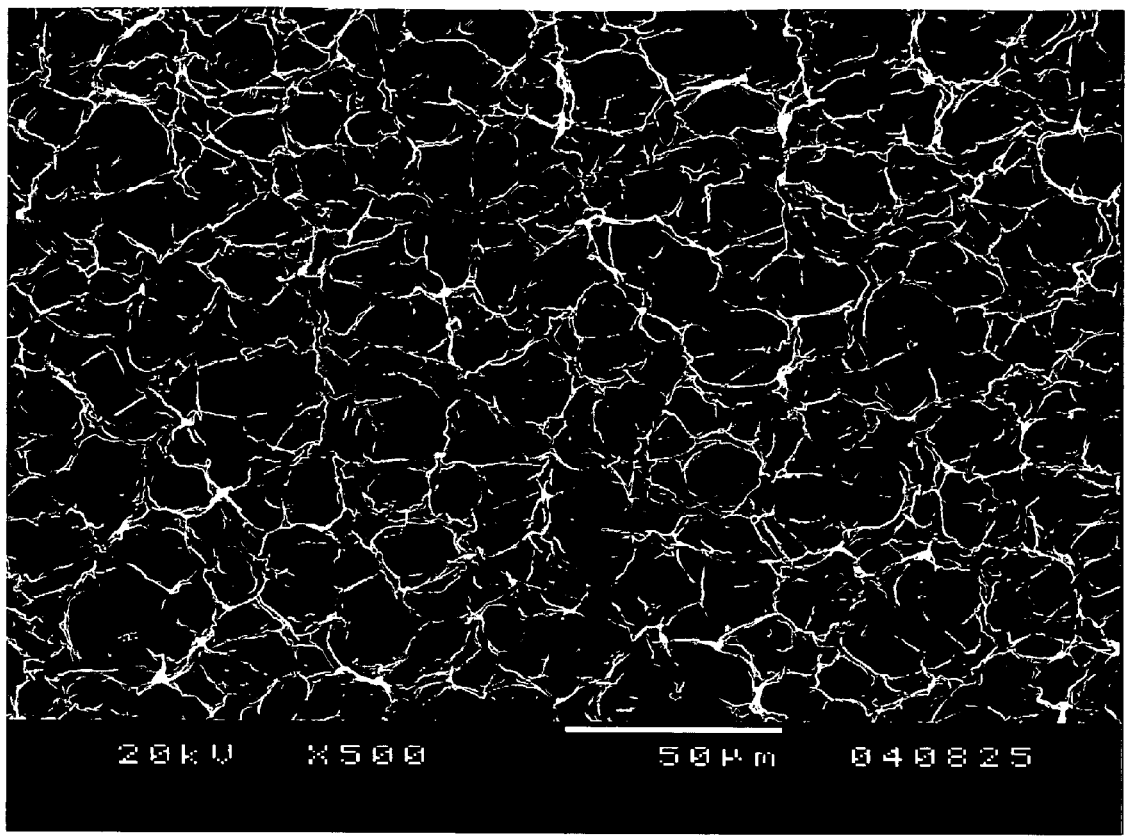
Fig. 8 an enlarged view of the surface of a crosslinked hyaluronic acid gel

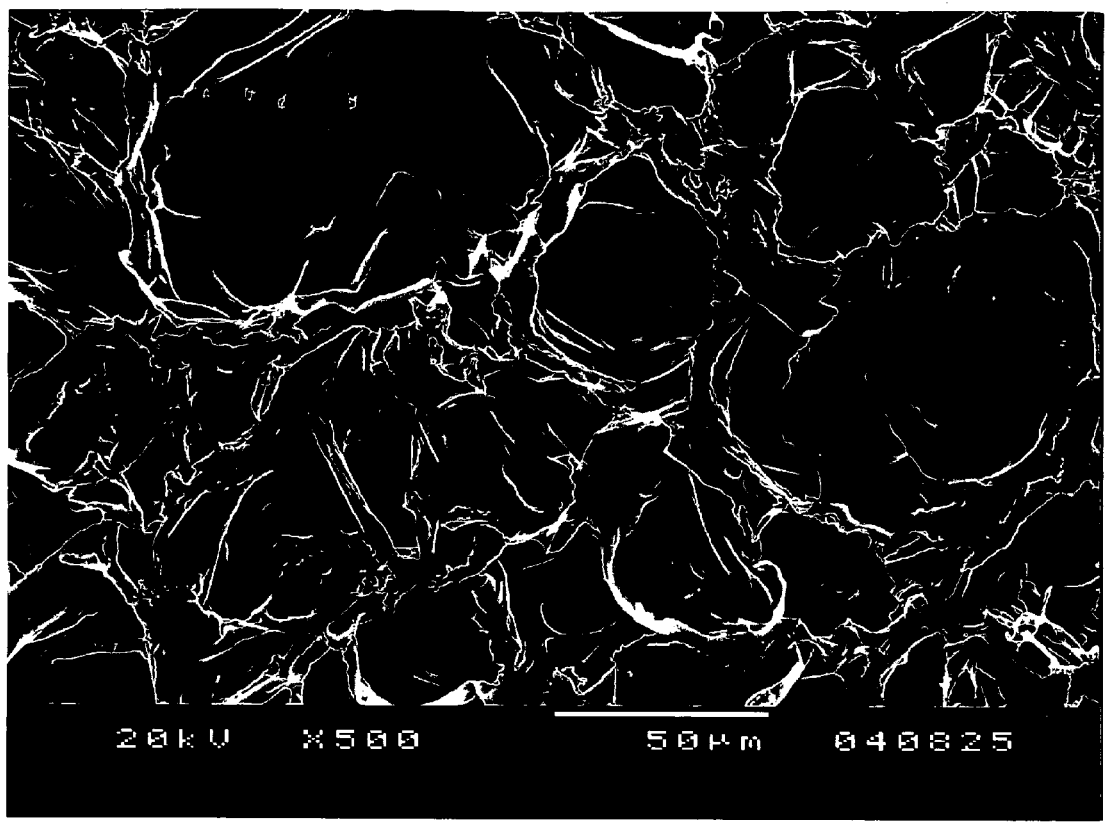
Fig. 9 an enlarged view of a section of the crosslinked hyaluronic acid gel

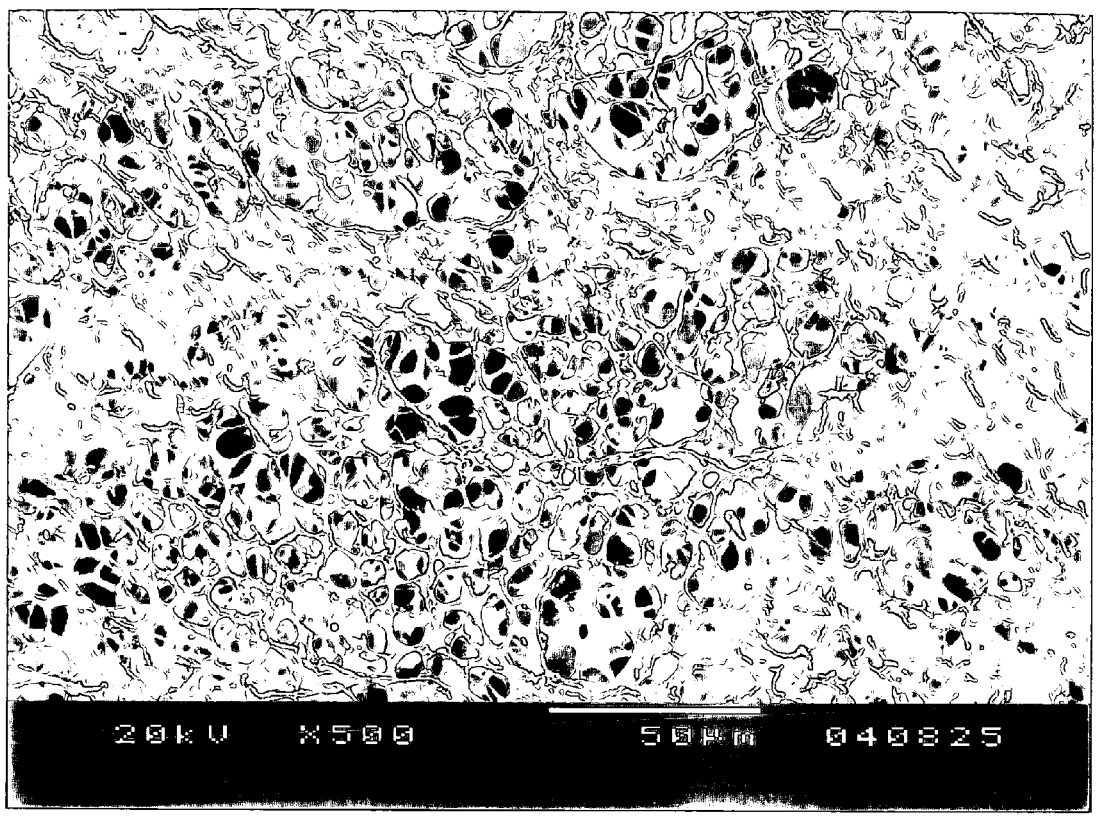
Fig. 10 an enlarged view of the surface of a crosslinked hyaluronic acid sponge

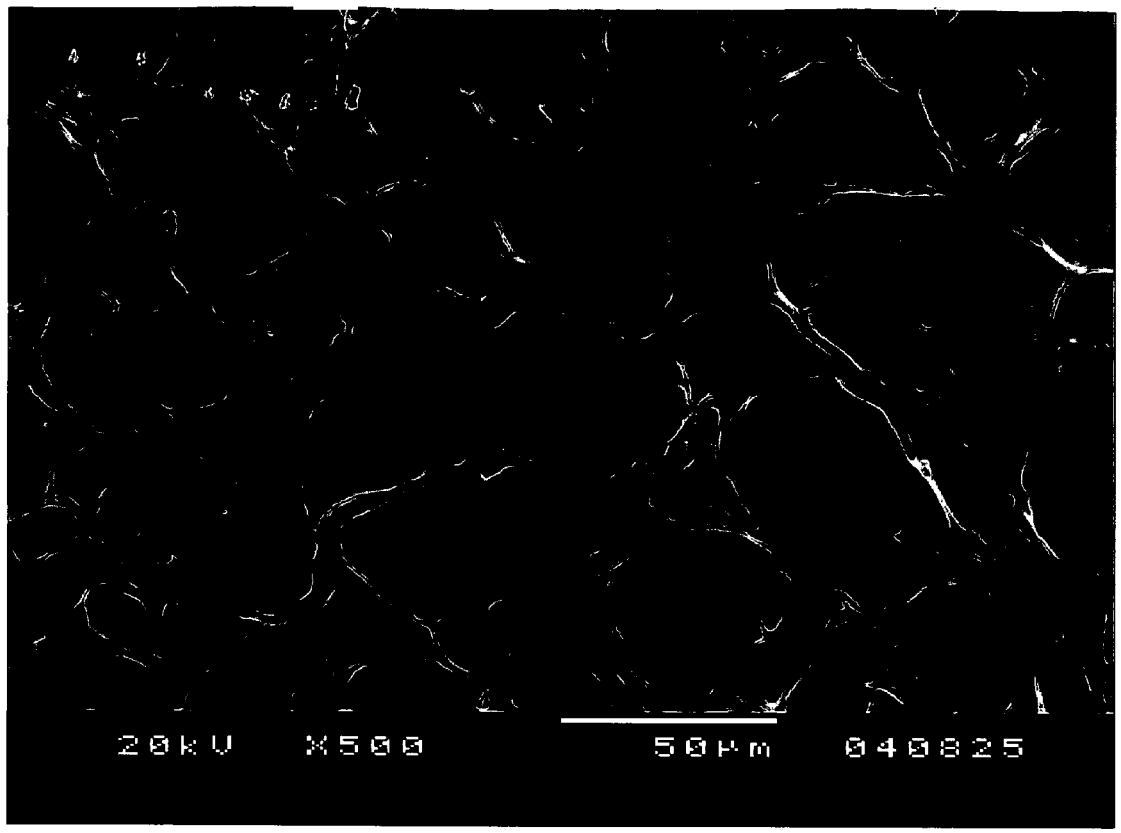
Fig. 11 an enlarged view of a section of the crosslinked hyaluronic acid sponge

POLYSACCHARIDE PSEUDO-SPONGE

This application is the US national phase of international application PCT/JP2004/013247, filed 10 Sep. 2004, which designated the U.S. and claims priority of JP 2003-322181, filed 12 Sep. 2003, the entire contents of each of which are hereby incorporated by reference.

TECHNICAL FIELD

The present invention relates to a polysaccharide pseudo-sponge, and more particularly, to a polysaccharide pseudo-sponge having combined properties of sponge and gel, which is produced by crosslinking reaction of photoreactive polysaccharide obtained by introducing a photoreactive group into polysaccharide.

BACKGROUND ART

Conventionally, there are known photoreactive polysaccharides obtained by introducing a photoreactive group into polysaccharides, as well as crosslinked polysaccharides obtained by crosslinking the photoreactive polysaccharides by irradiation of light such as ultraviolet rays (for example, Japanese Patent Application Laid-Open (KOKAI) Nos. 6-73102(1994), 8-143604(1996), 9-87236(1997) and 2002-249501). In addition, there are also known gels (polysaccharide gels) or sponges (polysaccharide sponges) produced from such crosslinked polysaccharides.

The polysaccharide gels have been produced by irradiating a solution of the photoreactive polysaccharide with light such as ultraviolet rays for crosslinking the photoreactive polysaccharide, and used, for example, as medical materials such as antiadhesive materials for inhibiting adhesion of tissues of living organisms (for example, Japanese Patent Application Laid-Open (TOKUHYO) No. 11-512778(1999)). Meanwhile, the above polysaccharide gels are obtained in the form of a solvated gel. When using an aqueous solution of photoreactive polysaccharides as a raw material, the resultant polysaccharide gels are in the form of a hydrogel due to hydration thereof. Such polysaccharide gels have a three-dimensional network structure, and therefore, are insoluble in water, but swelled up until reaching an equilibrium condition thereof in water.

On the other hand, the polysaccharide sponges are produced by freezing a solution of photoreactive polysaccharides and then irradiating the frozen solution with light such as ultraviolet rays to crosslink the photoreactive polysaccharides. In the production process, impurities such as crosslinking agents are extremely easily removed from the reaction mixture, thereby enabling production of high-purity products (for example, WO 02/060971 A1). Meanwhile, the term "sponge" means a porous substance having closed cells or interconnecting cells.

DISCLOSURE OF THE INVENTION

Problem to be Solved by the Invention

A hydrogel of crosslinked glycosaminoglycan as an example of polysaccharide gels has an excellent degradation ability in vivo. However, the hydrogel tends to be readily split when molded into a gel sheet, etc., and must be handled with a great care. In addition, due to a high swelling property of the hydrogel, it may be difficult to prevent displacement of the gel sheet when placed in vivo. Further, the problem concerning easy split of the gel sheet tend to become more remarkable due to the high swelling property, in particular, when used as an antiadhesive material in tissues of living organisms.

On the other hand, a sponge of the crosslinked glycosaminoglycan as an example of the polysaccharide sponges exhibits a low swelling property, and therefore, tends to be hardly displaced when placed in vivo. However, the polysaccharide sponges have a porous structure and a low degradation ability in vivo, and therefore, tend to easily undergo infiltration of cells, resulting in transformation of the sponges into a fibrous structure. Accordingly, the polysaccharide sponges are usable in vivo only in the specific limited applications such as scaffold for regeneration of tissues. Meanwhile, easy infiltration of cells into the polysaccharide sponges is considered to be due to a porosity thereof. The porosity (mesh size) of the polysaccharide sponges may be estimated from the degree of dyeing (dyeaffinity) with blue dextran which is generally considered to be hardly permeable into a network structure of the hydrogel. The polysaccharide sponges have a relatively large dyeaffinity.

The present invention has been conducted to solve the above problems. An object of the present invention is to provide a photocrosslinked polysaccharide having a novel physical structure, which can exhibit a low swelling property and a high degradation ability in vivo while retaining a suitable strength thereof.

Means For Solving The Problem

As a result of the present inventor's earnest study for solving the above problems and providing a photocrosslinked polysaccharide having a novel physical structure, which exhibits excellent combined properties of conventional crosslinked polysaccharide sponges and gels, it has been found that a specific polysaccharide pseudo-sponge obtained by imparting properties of polysaccharide gels to polysaccharide sponges having a low-swelling property, can realize a novel physical structure capable of overcoming defects of the conventional polysaccharide sponges. The present invention has been attained on the basis of the above finding. That is, the present invention includes the following plural aspects related to each other.

To accomplish the aim, in a first aspect of the present invention, there is provided a polysaccharide pseudo-sponge produced by a crosslinking reaction of a photoreactive polysaccharide obtained by introducing a photoreactive group into a polysaccharide, the said polysaccharide pseudo-sponge exhibiting a low swelling property and a blue dextran-low dyeaffinity which satisfy the following properties (I) and (II), respectively:

(I) a swelling ratio of not more than 125% as calculated from the values measured by immersing a test specimen having a thickness of 1 mm, a length of 10 mm and a width of 10 mm, and a solvent content of 96% by weight, in water for injection at room temperature for 1 hour, according to the following formula:

Swelling ratio=$\{(S2-S1)/S1\}\times 100$ wherein S1 represents an area of the test specimen before the immersion, and S2 is an area of the test specimen after the immersion, in which the area is calculated from the length and width of the test specimen; and (II) an absorbance of not more than 0.15 at a wavelength of 620 nm as measured with respect to an aqueous solution containing 0.67% by weight of a polysaccharide which is prepared by immersing a test specimen having a thickness of 1 mm, a length of 20 mm and a width of 10 mm, and a solvent content of 96% by weight, in an aqueous solution containing 0.5 g/mL of blue dextran having a weight-average molecular weight of 2,000,000, and then subjecting the test specimen to water-washing and hydrolysis.

In a second aspect of the present invention, there is provided a polysaccharide pseudo-sponge which is produced by irradiating light to a solution of a photoreactive polysaccharide obtained by introducing a photoreactive group into a polysaccharide to obtain a polysaccharide gel having a shape-retention property, freezing the obtained polysaccharide gel, and then irradiating light to the resultant frozen polysaccharide gel.

In a third aspect of the present invention, there is provided a polysaccharide pseudo-sponge which is produced by irradiating light to a solution of a photoreactive polysaccharide obtained by introducing a photoreactive group into a polysaccharide to obtain a polysaccharide gel having a shape-retention property, freeze-drying the obtained polysaccharide gel, and then irradiating light to the resultant freeze-dried polysaccharide gel.

In a fourth aspect of the present invention, there is provided a process for producing a polysaccharide pseudo-sponge, comprising the steps of irradiating light to a solution of a photoreactive polysaccharide obtained by introducing a photoreactive group into a polysaccharide to obtain a polysaccharide gel having a shape-retention property, freezing the obtained polysaccharide gel, and then irradiating light to the resultant frozen polysaccharide gel.

In a fifth aspect of the present invention, there is provided a process for producing a polysaccharide pseudo-sponge, comprising the steps of irradiating light to a solution of a photoreactive polysaccharide obtained by introducing a photoreactive group into a polysaccharide to obtain a polysaccharide gel having a shape-retention property, freeze-drying the obtained polysaccharide gel, and then irradiating light to the resultant freeze-dried polysaccharide gel.

In a sixth aspect of the present invention, there is provided a medical material comprising the above polysaccharide pseudo-sponge.

Effect of the Invention

In accordance with the present invention, there are provided a polysaccharide pseudo-sponge having not only an excellent biodegradability but also a good strength and a high barrier effect against adhesion in tissues, as well as a medical material using the polysaccharide pseudo-sponge.

BRIEF DESCRIPTION OF DRAWINGS

FIG. 6 is an enlarged view of the surface of a polysaccharide pseudo-sponge 2 according to the present invention.

FIG. 7 is an enlarged view of a section of a polysaccharide pseudo-sponge 2 according to the present invention.

FIG. 8 is an enlarged view of the surface of a crosslinked hyaluronic acid gel produced in Production Example 2(2).

FIG. 9 is an enlarged view of a section of the crosslinked hyaluronic acid gel produced in Production Example 2(2).

FIG. 10 is an enlarged view of the surface of a crosslinked hyaluronic acid sponge produced in Production Example 3(2).

FIG. 11 is an enlarged view of a section of the crosslinked hyaluronic acid sponge produced in Production Example 3(2).

PREFERRED EMBODIMENTS FOR CARRYING OUT THE INVENTION

Figure 1:
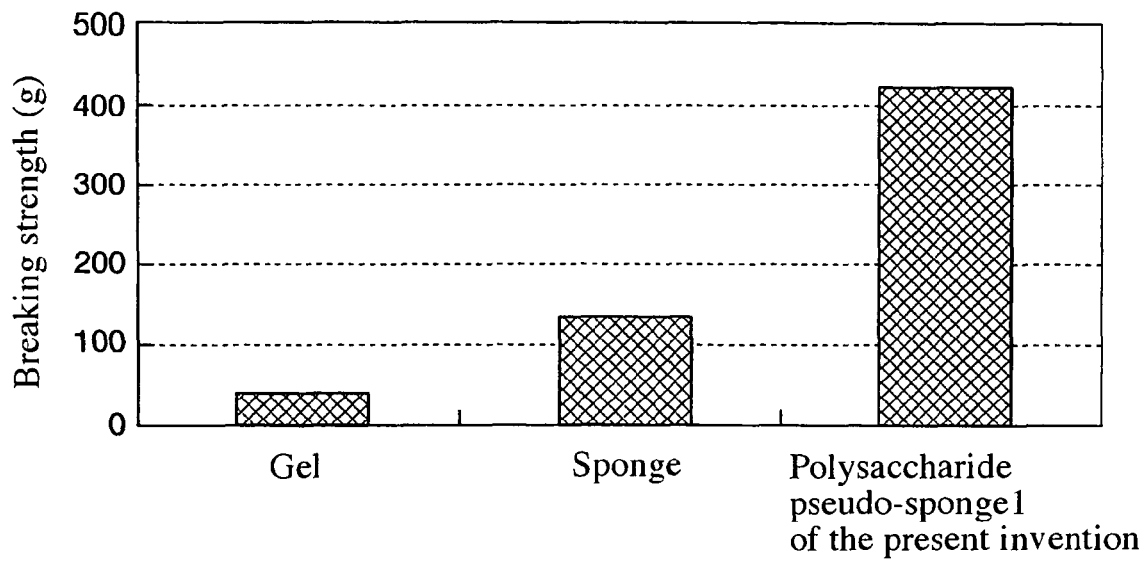
FIG. 1 is a graph showing a breaking strength of a polysaccharide pseudo-sponge 1 of the present invention.

The present invention is described in detail below. For the convenience of explanation, the process for producing a polysaccharide pseudo-sponge according to the present invention is first explained. In the present invention, similarly to the conventional photocrosslinked polysaccharides, a photoreactive polysaccharide obtained by introducing a photoreactive group into a polysaccharide is used as a raw material. The photoreactive polysaccharide can be produced by reacting the polysaccharide with a compound (photoreactive substance) capable of undergoing a photo-dimerization reaction or a photo-polymerization reaction therewith upon irradiation with light.

Examples of the polysaccharide may include homoglycan, heteroglycan and derivatives thereof. The homoglycan is a polysaccharide constituted from a single kind of monosaccharide solely. Examples of the homoglycan may include glucans such as amylose and cellulose; mannan; glycuronans such as pectic acid and alginic acid; polyglycosamines such as chitin and colominic acid; polygalactosamines; or the like. Among these homoglycans, preferred are glucans, and more preferred is cellulose.

Specific examples of the derivatives of homoglycans may include carboxymethylated derivatives such as carboxymethyl cellulose, hydroxymethylated derivatives such as hydroxymethyl cellulose, and de-acetylated derivatives such as chitosan. Among these derivatives of homoglycans, preferred are water-soluble derivatives, more preferred are carboxymethylated derivatives, in particular, carboxymethyl cellulose, and hydroxymethylated derivatives, in particular, hydroxymethyl cellulose, and still more preferred are carboxymethylated homoglycans.

The heteroglycan is a polysaccharide constituted from two kinds of sugars. Among the heteroglycans, preferred are glycosaminoglycan or derivatives thereof. Specific examples of the glycosaminoglycan may include hyaluronic acid, chondroitin, chondroitin sulfate, dermatan sulfate, heparin, heparan sulfate, keratan sulfate or the like. Specific examples of the glycosaminoglycan derivatives may include sulfated derivatives such as sulfated hyaluronic acid and chondroitin polysulfate; de-sulfated derivatives such as de-sulfated heparin; and oxidation-reduction derivatives such as periodic acid oxidation-reduction heparin and periodic acid oxidation-reduction de-sulfated heparin (Japanese Patent Application Laid-Open (KOKAI) No. 11-310602(1999)). Examples of the de-sulfated heparin may include 6-position de-sulfated heparin (WO 00/06608 A1) and 2-position de-sulfated heparin (Japanese Patent Application Laid-Open (KOKAI) No. 2003-113090).

The weight-average molecular weight of the polysaccharide used in the present invention varies depending upon kinds thereof. When hyaluronic acid is used as the polysaccharide, the weight-average molecular weight of the hyaluronic acid is usually 200,000 to 3,000,000, preferably 300,000 to 2,000,000, more preferably 400,000 to 1,200,000, and when other sugars are used as the polysaccharide, the weight-average molecular weight thereof is usually 4,000 to 2,500,000.

The photoreactive group may be a residue of a compound (photoreactive substance) having a photoreactive crosslinking group or a photoreactive unsaturated bond, which is capable of undergoing a photo-dimerization reaction or a photo-polymerization reaction by irradiation with light such as ultraviolet rays to form a crosslinked structure. Meanwhile, the kind of photoreactive group is not particularly limited as long as it can undergo polymerization or dimerization upon irradiation with light, and unless glycoside bond of the polysaccharide is cut or broken by introducing the photoreactive group thereinto.

Examples of the photoreactive substance may include cinnamic acid, substituted cinnamic acids such as aminocinnamic acid formed by replacing any hydrogen atom bonded to a benzene ring of cinnamic acid with an amino group, preferably p-aminocinnamic acid; acrylic acid; maleic acid; fumaric acid; furyl-acrylic acid; thiophene-acrylic acid; cinnamylidene-acetic acid; sorbic acid; thymine; coumarin; and derivatives thereof. Among these photoreactive substances, cinnamic acid, substituted cinnamic acids and derivatives thereof are preferred in the consideration of safety.

In addition, a spacer may be bonded to the photoreactive substance to enhance a photoreactivity thereof and facilitate the photo-crosslinking reaction or the reaction for introducing the photoreactive group into the polysaccharide. The spacer is preferably a divalent or polyvalent functional compound having a chain-like or cyclic hydrocarbon residue having 2 to 18 carbon atoms. For example, in the case where cinnamic acid is used as the photoreactive substance, the spacer is preferably amino alcohol having 2 to 8 carbon atoms. In this case, the amino alcohol is ester-bonded or amide-bonded to a carboxyl group of the cinnamic acid. More preferably, the spacer is n-amino propanol or n-amino butanol.

The photoreactive polysaccharide may be produced by known methods as described, for example, in Japanese Patent Application Laid-Open (KOKAI) Nos. 6-73102(1994) and 8-143604(1996), Japanese Patent Application Laid-Open (TOKUHYO) No. 11-512778(1999), etc.

In the process of the present invention, the photoreactive polysaccharide is used in the form of a solution thereof. Here, the "solution" means a liquid in which the photoreactive polysaccharide is dissolved or uniformly dispersed. The solvent used for preparing the photoreactive polysaccharide solution is not particularly limited as long as the solution can be frozen or freeze-dried after irradiating light thereto while keeping the photoreactive polysaccharide dissolved or dispersed therein. The solvent is preferably an aqueous solvent. Examples of the aqueous solvent may include a phosphate buffered saline, distilled water, water for injection, etc.

The concentration of the photoreactive polysaccharide in the solution may be appropriately determined according to the relationship between a molecular weight of the polysaccharide and a degree of substitution of the photoreactive group, and is usually 0.1 to 10% by weight. For example, when the photoreactive group is introduced at a degree of substitution of 0.1 to 15% into hyaluronic acid having a weight-average molecular weight of 400,000 to 1,200,000, the concentration of the photoreactive polysaccharide in the solution is preferably 0.5 to 8% by weight.

Meanwhile, the "degree of substitution of the photoreactive group" means the value by percentage which is calculated from a ratio of a number of moles of the "photoreactive group introduced" (number of the photoreactive substances introduced) to a number of moles of "functional groups into which the photoreactive group can be introduced" which is contained in the polysaccharide. The functional group of the polysaccharide into which the photoreactive group can be introduced, may vary depending upon kind of the photoreactive group or spacer. When a carboxyl group contained in the photoreactive group or spacer is to be bonded to the polysaccharide, examples of the functional group of the polysaccharide may include an amino group and a hydroxyl group. Whereas, when an amino or hydroxyl group contained in the photoreactive group or spacer is to be bonded to the polysaccharide, examples of the functional group of the polysaccharide may include a carboxyl group.

Before subjecting the photoreactive polysaccharide solution to crosslinking reaction by irradiation with light, substances other than the photoreactive polysaccharide and solvent such as unreacted photoreactive substance, impurities and foreign materials are preferably removed therefrom, thereby enhancing a purity of the resultant polysaccharide pseudo-sponge of the present invention to such an extent that the sponge is usable in medical applications such as medical equipments. The removal of the impurities and foreign materials, etc., which are contained in the solution may be conducted, for example, by ordinary methods such as dialysis, filtration and centrifugal separation. The photoreactive polysaccharide is usually produced in the form of an aqueous solvent solution. Therefore, the photoreactive substance which is unreacted with the polysaccharide can be extremely easily removed from the solution. Such a removal treatment is very advantageous, in particular, for producing the polysaccharide pseudo-sponge of the present invention which is difficult to clean.

Next, the photoreactive polysaccharide solution is irradiated with light to obtain a polysaccharide gel having a shape-retention property. Then, the obtained polysaccharide gel is frozen or freeze-dried, and the resultant frozen or freeze-dried product of the polysaccharide gel is further irradiated with light.

The light irradiation is preferably conducted through a container used for retaining a shape of the solution. In particular, such a container is preferably used upon irradiating light to the frozen polysaccharide gel. The shape of the container is usually determined in the consideration of the shape of the finally obtained polysaccharide pseudo-sponge of the present invention. In this case, for example, when using a photoreactive polysaccharide produced by using a photoreactive substance having an unsaturated double bond which is capable of undergoing a crosslinking reaction upon absorption of ultraviolet rays, such as cinnamoyl group (residue of cinnamic acid), since ultraviolet rays tend to be absorbed by water used as a solvent in the crosslinking reaction, the light irradiation is preferably controlled such that an optical path length of the ultraviolet rays is not more than 1 cm. It is required that the material of the container is selected from those materials incapable of absorbing light required for the crosslinking reaction of the photoreactive polysaccharide, i.e., capable of allowing such a light to penetrate therethrough. Examples of the material of the container which is suitably used in the crosslinking reaction using ultraviolet rays may include polymer compounds such as polypropylene having a low ultraviolet absorptivity, glass such as quartz glass and hard glass, etc. Meanwhile, when irradiating light to the freeze-dried product, the use of the container is not necessarily required, and light may be directly irradiated onto the freeze-dried product.

The light irradiated is not particularly limited as long as the photoreactive substance undergoes the reaction such as polymerization and dimerization. Examples of the light irradiated which is involved in the present invention may include visible light, ultraviolet rays, infrared rays, electron beams and radiation rays. Among these light and rays, preferred are visible light and ultraviolet rays, and more preferred are ultraviolet rays. The wavelength of the light used is preferably 180 to 650 nm. For example, in the case where cinnamic acid is used as the photoreactive substance, there may be suitably used ultraviolet rays having a wavelength of 260 to 350 nm. Suitable irradiation conditions for obtaining the polysaccharide gel having a shape-retention property may be conveniently determined by conducting preliminary experiments.

The freezing conditions used for freezing the polysaccharide gel obtained by irradiating the photoreactive polysaccharide solution with light, are not particularly limited as long as the polysaccharide gel is suitably frozen thereunder, and the polysaccharide gel can be frozen by conventionally known methods ordinarily used for production of polysaccharide sponges. For example, the polysaccharide gel may be rapidly frozen using an ultra-low temperature substance such as liquid nitrogen, or a cooling medium cooled below a freezing point of the polysaccharide gel such as ethanol. Alternatively, the polysaccharide gel may be relatively slowly frozen by cooling the gel using general domestic refrigerators. Meanwhile, the freezing treatment may be usually successively conducted after the step of producing the polysaccharide gel. The polysaccharide gel accommodated in the container may be directly cooled. Also, when the polysaccharide gel obtained by irradiating the photoreactive polysaccharide solution with light, is freeze-dried, there may be used ordinary freeze-drying methods. For example, there may be used the method of freezing the polysaccharide gel at −20° C., and then freeze-drying the frozen product at room temperature under reduced pressure, e.g., under 1 pascal (Pa).

It is known that the frozen or freeze-dried product undergoes a crosslinking reaction with a remarkably small amount of light energy as compared to that required for crosslinking reaction of a solution. Therefore, it is economically advantageous that production of the polysaccharide gel having a shape-retention property before the freezing or freeze-drying treatment is conducted by irradiating a minimum necessary amount of light, and a sufficient light irradiation for attaining the aimed crosslinking ratio is conducted after the freezing or freeze-drying treatment.

The amount of light irradiated may appropriately vary depending upon aimed applications of the polysaccharide pseudo-sponge of the present invention. Here, the "amount of light" is calculated from a product of an "illuminance per unit area" and an "irradiation time". For example, in the case where aminopropyl cinnamate obtained by bonding amino propanol to cinnamic acid and hyaluronic acid is used as the photoreactive substance and polysaccharide, respectively, the following procedure may be conducted in order to obtain the polysaccharide pseudo-sponge of the present invention which exhibits a relatively high mechanical strength.

First, an aqueous solution containing, for example, 4% by weight of photoreactive hyaluronic acid having 8% as a degree of substitution of photoreactive group is filled in a container capable of allowing the solution to be irradiated with light from both sides thereof, and light is irradiated to the solution from both sides of the container in an amount of 50 J/cm² per one side thereof (measuring wavelength: 280 nm) to obtain a polysaccharide gel having a shape-retention property. Next, the thus obtained polysaccharide gel is frozen, and light is irradiated to the frozen gel from both sides thereof in an amount of 100 to 250 mJ/cm² per one side thereof (measuring wavelength: 280 nm), thereby obtaining a photocrosslinked hyaluronic acid pseudo-sponge. Meanwhile, when using a 3 kw high-pressure mercury lamp, the light irradiation only from one side is possible. In such a case, in order to compensate unevenness of light irradiation, the container filled with the aqueous solution containing a photoreactive hyaluronic acid or the frozen gel is turned every irradiation of light, thereby allowing the frozen gel to be irradiated with light from both sides thereof.

The total amount of light irradiated, for example, upon producing the polysaccharide gel may be not less than about 1,000 mJ/cm², and is preferably 100,000 mJ/cm². Further, in order to obtain the pseudo-sponge of the present invention by irradiating light to the frozen polysaccharide gel, the total amount of light to be irradiated to the frozen polysaccharide gel may be not less than 10 mJ/cm², and is preferably 500 mJ/cm². In the case where the polysaccharide gel obtained by irradiating the photoreactive polysaccharide solution with light is freeze-dried, since the light transmittance of the freeze-dried polysaccharide gel is lower than that of the frozen product, the total amount of light to be irradiated is usually not less than 500 mJ/cm², preferably not less than 5 J/cm², more preferably not less than 10 J/cm².

Meanwhile, the amount of light irradiated may be measured, for example, using an illuminance meter "UV-M10" (manufactured by ORC Manufacturing Co., Ltd.), but may also be measured by ordinary apparatuses capable of irradiating a similar amount of light.

In addition, in the production method of the present invention, the photoreactive polysaccharide solution may also comprise any material (additive) exhibiting a miscibility with an aqueous solvent which is selected from the group consisting of alcohols, surfactants and chelating agents. For example, after dissolving the photoreactive polysaccharide and the above additive in the aqueous solvent to prepare a photoreactive polysaccharide solution, the resultant solution may be irradiated with light to obtain a polysaccharide gel having a shape-retention property. Then, after freezing or freeze-drying the obtained polysaccharide gel, the thus obtained frozen or freeze-dried product may be irradiated with light to obtain the polysaccharide pseudo-sponge of the present invention.

Meanwhile, the additive having a miscibility with the aqueous solvent which is selected from the group consisting of alcohols, surfactants and chelating agents, must be selected from those materials incapable of inhibiting functions or effect of the polysaccharide pseudo-sponge of the present invention. Examples of the alcohols having a miscibility with the aqueous solvent may include those alcohols, in particular, polyethyleneglycols, which are represented by the following general formula (1):

$$R\text{—}OH \tag{1}$$

wherein R is any group selected from the group consisting of the following groups (a) to (e):
(a) a chain-like alkyl group having 1 to 10 carbon atoms;
(b) a branched alkyl group having 3 to 10 carbon atoms;
(c) —CH$_2$—(CHOH)$_l$—CH$_2$OH, wherein l is an integer of 0 to 5;

wherein m is an integer of 3 to 5; and (e) —(CH$_2$CH$_2$O)$_n$—H, wherein n is an integer of 3 to 70.

Examples of the chain-like alkyl group having 1 to 10 carbon atoms may include methyl, ethyl or the like. Examples of the branched alkyl group having 3 to 10 carbon atoms may include isopropyl, t-butyl or the like.

Examples of the above alcohols may include lower alcohols, polyhydric alcohols and sugar alcohols.

Examples of the lower alcohols may include alcohols having 1 to 10 carbon atoms, preferably 1 to 8 carbon atoms. Specific examples of the lower alcohols may include methanol, ethanol, isopropanol, t-butyl alcohol or the like. The polyhydric alcohols are alcohols containing 2 or more hydroxyl groups, preferably 3 or more hydroxyl groups, in a molecule thereof. Specific examples of the polyhydric alcohols may include ethyleneglycol and glycerol. Among these polyhydric alcohols, preferred is ethyleneglycol. Also, the sugar alcohols usable in the present invention may be either chain-like sugar alcohols or cyclic sugar alcohols, preferably chain-like alcohols. Examples of the sugar alcohols may include inositol, mannitol, xylitol, sorbitol or the like. Among these sugar alcohols, preferred are mannitol, xylitol and sorbitol, and more preferred are mannitol and sorbitol.

As the surfactants, there are preferably used nonionic surfactant and anionic surfactants. Examples of the nonionic surfactants may include polyethyleneglycol (PEG). Examples of the anionic surfactants may include salts of alkylsulfuric acids, preferably sodium dodecylsulfate.

Examples of the chelating agents may include oxycarboxylic acids such as citric acid, and polyaminocarboxylic acids such as edetic acids, e.g., salts of ethylenediaminetetraacetic acid (EDTA).

The additive having a miscibility with the aqueous solvent which is selected from the group consisting of the above alcohols, surfactants and chelating agents, may be suitably selected according to properties or applications of the obtained polysaccharide pseudo-sponge. For example, the polysaccharide pseudo-sponge produced according to the process of the present invention using citric acid as the additive can be enhanced in strength and adhesion property when formed into a sheet shape. Also, the polysaccharide pseudo-sponge obtained by adding any of glycerol and polyethyleneglycol 400 (PEG 400) thereto can be enhanced in flexibility when formed into a sheet shape. Further, as mentioned below, in the case where the polysaccharide pseudo-sponge of the present invention is used as a medical material for sustained release of drugs by previously impregnating the drugs thereinto, for example, in order to impregnate the polysaccharide pseudo-sponge with lipid-soluble drugs, glycerol and PEG 400 may be suitably selected as the additive, and EDTA may be suitably selected as the additive for impregnating the polysaccharide pseudo-sponge with a basic fibroblast growth factor.

Next, the polysaccharide pseudo-sponge of the present invention is explained. As described above, the polysaccharide pseudo-sponge of the present invention is produced by subjecting the photoreactive polysaccharide obtained by introducing a photoreactive group into a polysaccharide to crosslinking reaction. The polysaccharide pseudo-sponge of the present invention is characterized by exhibiting a low swelling property and a blue dextran-low dyeaffinity which satisfy the following properties (I) and (II), respectively:

(I) a swelling ratio of not more than 125% as calculated from the values measured by immersing a test specimen having a thickness of 1 mm, a length of 10 mm and a width of 10 mm, and a solvent content of 96% by weight, in water for injection at room temperature for 1 hour, according to the following formula:

$$\text{Swelling ratio} = \{(S2-S1)/S1\} \times 100$$

wherein S1 represents an area of the test specimen before the immersion, and S2 is an area of the test specimen after the immersion, in which the area is calculated from the length and width of the test specimen; and (II) an absorbance of not more than 0.15 at a wavelength of 620 nm as measured with respect to an aqueous solution containing 0.67% by weight of a polysaccharide which is prepared by immersing a test specimen having a thickness of 1 mm, a length of 20 mm and a width of 10 mm, and a solvent content of 96% by weight, in an aqueous solution containing 0.5 g/mL of blue dextran having a weight-average molecular weight of 2,000,000, and then subjecting the test specimen to water-washing and hydrolysis.

The polysaccharide pseudo-sponge of the present invention which is produced by irradiating a photoreactive polysaccharide solution with light to obtain a polysaccharide gel, freezing the polysaccharide gel, and then irradiating the thus obtained frozen polysaccharide gel with light, exhibits the same solvation condition as that of conventional polysaccharide gels, i.e., the polysaccharide pseudo-sponge of the present invention may be produced in a solvent-containing state. When an aqueous solution of the photoreactive polysaccharide is used as the raw material, the polysaccharide pseudo-sponge may be produced in a hydrous state. Thus, when the aqueous solution of the photoreactive polysaccharide is used as the photoreactive polysaccharide solution upon producing the polysaccharide pseudo-sponge of the present invention, the above solvent content means a water content thereof. That is, for example, when using a 4 wt % aqueous solution of cinnamic acid-introduced hyaluronic acid, there is obtained a polysaccharide pseudo-sponge containing 96% by weight of water, namely, the solvent content (water content) thereof is 96% by weight. Meanwhile, a polysaccharide pseudo-sponge obtained by drying the above hydrous polysaccharide pseudo-sponge is also involved in the scope of the present invention.

On the other hand, the polysaccharide pseudo-sponge of the present invention which is produced by irradiating the photoreactive polysaccharide solution with light to obtain a polysaccharide gel, freeze-drying the polysaccharide gel and then irradiating the thus obtained freeze-dried polysaccharide gel with light, contains no solvent such as water unlike the above solvent-containing polysaccharide pseudo-sponge. However, the solvent-free polysaccharide pseudo-sponge may be immersed in a solvent such as water to obtain the solvent-containing polysaccharide pseudo-sponge. For example, a test specimen used for examining properties of the polysaccharide pseudo-sponge (water content: 96% by weight) may be prepared by immersing a water-free sample in distilled water used in an amount 24 times a weight of the sample to cause the sample to absorb water, and then cut the water-impregnated sample into a desired size. In addition, there may also be used such a test specimen which is produced by previously molding the polysaccharide gel into a desired size before freeze-drying. Meanwhile, the test for low swelling property may be conducted by comparing a size of a test specimen before freeze-drying, which is prepared by previously molding the polysaccharide gel into a size of 1 cm in length×1 cm in width×1 mm in thickness, with a size of the same test specimen which is allowed to absorb a sufficient amount of distilled water after freeze-drying.

As described above, the low swelling property in water is inherent to polysaccharide sponges. That is, although the polysaccharide gel is swelled up by solvation, the polysaccharide sponges undergo substantially no swelling (this property is not largely influenced by a crosslinking ratio thereof). The polysaccharide pseudo-sponge of the present invention exhibits a low swelling property, i.e., a swelling ratio of not more than 125% as measured by the above swelling test (I), which is similar to that of the polysaccharide sponges. The swelling ratio of the polysaccharide pseudo-sponge of the present invention is preferably not more than 100%, more preferably not more than 70%. The much lower swelling property of the polysaccharide pseudo-sponge can be achieved, for example, by enhancing a crosslinking ratio thereof.

In the above blue dextran-dyeaffinity test (II), water for injection is usually used for preparing an aqueous blue dextran solution. Also, the test specimen of the polysaccharide pseudo-sponge is hydrolyzed for 1 hour by adding 1 mL of 1 mol/L NaOH thereto. Upon the hydrolysis, a whole portion of the test specimen is dissolved, thereby preparing a polysaccharide solution containing the dye used for tinting the test specimen. The absorbance of the polysaccharide solution may be measured using a spectrophotometer.

In the present invention, as the method for tinting the test specimen with blue dextran, the following two methods may be used for ensuring formation of the tinted test specimen. One of the methods is a so-called soaking method in which the test specimen is immersed in 1 mL of a blue dextran solution for 1 hour, taken out from the solution, and then lightly rinsed in water for injection; and the other method is a so-called dipping method in which after repeating the operation of suspending and dipping the test specimen in a blue dextran solution 10 times, the operation of suspending and dipping the test specimen in water for injection is repeated 10 times. In the former method, the test specimen is tinted or dyed over a sufficient period of time, whereas in the latter method, the test specimen is tinted or dyed while preventing swelling thereof.

Meanwhile, since the polysaccharide sponge inherently has a high blue dextran dyeaffinity, it is not essentially expectable that the polysaccharide sponge can exhibit a low dyeaffinity with blue dextran. Rather, since it is generally considered that blue dextran cannot be penetrated into a network structure of a hydrogel, the low dyeaffinity with blue dextran is a property exhibited by the polysaccharide gel. However, the polysaccharide pseudo-sponge of the present invention exhibits such a low dyeaffinity that an absorbance thereof is not more than 0.15 as measured by the above method shown in the below-mentioned Examples. Such a low dyeaffinity of the polysaccharide pseudo-sponge of the present invention is considered to be due to polysaccharide gel-like properties thereof. The absorbance of the polysaccharide pseudo-sponge according to the present invention as measured by the dyeaffinity test is preferably not more than 0.10, more preferably not more than 0.05. A much lower dyeaffinity of the polysaccharide pseudo-sponge can be achieved by enhancing a crosslinking ratio thereof. Meanwhile, the blue dextran dyeaffinity is considered to have a correlation with a barrier effect of preventing adhesion of tissues or cells in vivo, and therefore, is usable as an index for estimating the barrier effect. Thus, the low blue dextran dyeaffinity of the polysaccharide pseudo-sponge of the present invention suggests a high barrier effect of the polysaccharide pseudo-sponge for inhibiting the adhesion of tissues, etc.

The polysaccharide pseudo-sponge of the present invention preferably has a breaking strength of not less than 200 g as measured by piercing and breaking a test specimen having a thickness of 1 mm, a length of 60 mm and a width of 25 mm, and a solvent content of 96% by weight, with a 12.7 mm-diameter spherical probe at 24° C. and a piercing speed of 1 mm/s by using a texture analyzer. Such a high breaking strength of the polysaccharide pseudo-sponge cannot be achieved even by conventional polysaccharide sponges as shown in the below-mentioned Examples, and therefore, is one of unique properties exhibited by the polysaccharide pseudo-sponge of the present invention. The breaking strength of the polysaccharide pseudo-sponge obtained by the method of irradiating the frozen polysaccharide gel with light is preferably not less than 250 g, more preferably not less than 300 g, whereas the breaking strength of the polysaccharide pseudo-sponge obtained by the method of irradiating the freeze-dried polysaccharide gel with light is preferably not less than 210 g, more preferably not less than 220 g. The higher breaking strength of the polysaccharide pseudo-sponge can be achieved by enhancing a crosslinking ratio thereof.

The polysaccharide pseudo-sponge of the present invention preferably has an enzymatic degradation time of not more than 1300 minute as measured at 50° C. by subjecting a test specimen having a thickness of 1 mm, a length of 20 mm and a width of 10 mm, and a solvent content of 96% by weight, to a polysaccharide degrading enzyme (e.g., hyaluronidase) in a reaction mixture containing 1 mL of a 5 mmol/L phosphate buffered saline, 0.2 mL of a 1 mol/L acetate buffer solution and 0.2 mL of a 5TRU (Turbidity Reducing Unit)/mL the enzyme solution. The enzymatic degradation time of the polysaccharide pseudo-sponge of the present invention is preferably not more than 1,250 min, more preferably not more than 1,200 min, still more preferably not more than 1,000 min. The above-specified enzymatic degradation time of the polysaccharide pseudo-sponge can be achieved, for example, by controlling a crosslinking ratio thereof.

The polysaccharide pseudo-sponge of the present invention is characterized by exhibiting combined properties of polysaccharide sponge and polysaccharide gel as is apparent from the above low swelling property and the low blue dextran dyeaffinity thereof. The reason why the polysaccharide pseudo-sponge of the present invention have such unique properties, is considered as follows, though not clearly determined.

That is, as described above, the frozen or freeze-dried product tends to readily undergo crosslinking reaction with a remarkably small amount of light energy as compared to that required for crosslinking reaction of a solution. In addition, the frozen product is more readily subjected to crosslinking reaction as the freezing temperature thereof is lowered. It is considered that such a high crosslinking efficiency is due to phase separation of the photoreactive polysaccharide solution into a solvent and a solute thereof, enhanced orientation (crystallinity) of the photoreactive polysaccharide molecules, lowering of thermal motion, etc. Meanwhile, the polysaccharide pseudo-sponge of the present invention is obtained by two-stage crosslinking reaction including a first-stage crosslinking reaction conducted in a solution state and a second-stage crosslinking reaction conducted in a frozen or freeze-dried state. In this case, for example, the following phenomena are suggested.

(a) In the first-stage slow crosslinking reaction, a small amount of a three-dimensional network structure is formed. Then, in the second-stage crosslinking reaction conducted in a frozen or freeze-dried state, there is formed such a dense structure in which the photoreactive polysaccharide molecules are arranged within the three-dimensional network structure. As a result, there is formed a composite structure in which coarse and dense portions are three-dimensionally arranged, for example, like a reinforced concrete construction.

(b) In the first-stage slow crosslinking reaction, the three-dimensional network structure is totally formed, and after thus enhancing orientation of the photoreactive polysaccharide molecules, the second-stage crosslinking reaction is conducted in a frozen or freeze-dried state. As a result, as compared to the case where orientation of the photoreactive polysaccharide molecules is made only in the second-stage crosslinking reaction in a frozen or freeze-dried state, there can be formed such a high orientation structure in which the three-dimensional orientation of the photoreactive polysaccharide molecules is further enhanced.

In any case, it is considered that the polysaccharide pseudo-sponge of the present invention has a different structure from those of conventional polysaccharide sponges and polysaccharide gels owing to the above unique properties thereof. Further, it is considered that the polysaccharide pseudo-sponge of the present invention has a high breaking strength which is unachievable even by the conventional polysaccharide sponges owing to the above composite structure (a) and/or high orientation structure (b).

Next, the medical material of the present invention is explained. The medical material of the present invention is characterized by comprising the above polysaccharide pseudo-sponge of the present invention. In the process for production of the polysaccharide pseudo-sponge of the present invention, impurities or foreign materials are readily removed therefrom as described above. In particular, the polysaccharides such as glycosaminoglycan are present in vivo. Therefore, it is considered that the polysaccharide pseudo-sponge of the present invention exhibits a high safety when used in vivo, thereby enabling the polysaccharide pseudo-sponge to be used as a medical material. Specific examples of the medical material may include an antiadhesive material used in tissues of living organisms, for example, post-operative antiadhesive materials used upon operation.

Meanwhile, in the case where the antiadhesive material has a high swelling property, the antiadhesive material tends to be displaced from the aimed region where adhesion of tissues is to be inhibited, resulting in poor antiadhesive effect. For example, a sheet-like antiadhesive material having a high swelling property tends to be deteriorated in strength upon swelling, resulting in easy split and breakage upon application of an external pressure thereto. As a result, there tends to be caused such a significant problem that the material no longer acts as a barrier for keeping tissues apart from each other. On the other hand, since the polysaccharide pseudo-sponge of the present invention has an extremely low swelling property, the antiadhesive material obtained therefrom can be hardly displaced from the aimed region. In addition, the antiadhesive material of the present invention undergoes substantially no split and breakage even when used in the form of a sheet, and therefore, is very useful as a barrier material. Since the polysaccharide pseudo-sponge of the present invention is readily degraded in vivo, there is caused no problem that the antiadhesive material stays in vivo for a too long period of time. Further, due to the above low blue dextran dyeaffinity, the polysaccharide pseudo-sponge of the present invention is considered to exhibit a good resistance to infiltration of cells. Such a property is suitable, in particular, as antiadhesive materials.

Also, examples of the other medical material may include a base material for sustained release of drugs. More specifically, the polysaccharide pseudo-sponge of the present invention, which exhibits an excellent degradation ability in vivo can be used as a base material for sustained release of drugs by previously impregnating drugs thereinto. Such a medical material for sustained release of drugs may be produced by previously mixing drugs in the photoreactive polysaccharide solution upon producing the polysaccharide pseudo-sponge of the present invention. Alternatively, the base material for sustained release of drugs may also be produced by simply impregnating the polysaccharide pseudo-sponge of the present invention with drugs.

Examples of the drugs which can be contained in the polysaccharide pseudo-sponge of the present invention may include non-steroidal anti-inflammatory drugs such as indomethacin, mefenamic acid, acemethacin, alclofenac, ibuprofen, thiaramide hydrochloride, fenbufen, mepirizole and salicylic acid; anti-malignant tumor drugs such as methotrexate, fluorouracil, vincristine sulfate, mitomycin C, actinomycin C and daunorubicin hydrochloride; antiulcer drugs such as aceglutamide aluminum, L-glutamine, P-(trans-4-aminomethylcyclohexanecarbonyl)-phenyl propionic acid hydrochloride, cetraxate hydrochloride, sulpiride, gefarnate, cimetidine, ranitidine and famotidine; enzyme preparations such as chymotrypsin, streptokinaze, lysozyme chloride, bromelain, urokinase and tissue plasminogen activator; antihypertensive drugs such as clonidine hydrochloride, bunitrolol hydrochloride, prazosin hydrochloride, captopril, bethanidine sulfate, metoprolol tartrate and methyldopa; urogenital drugs such as flavoxate hydrochloride; antithrombus drugs such as heparin, heparan sulfate, thrombomodulin, dicumarol and waffarin; antiarteriosclerosis drugs such as clofibrate, simfibrate, elastase and nicomol; circulatory drugs such as nicardipine hydrochloride, nimodipine hydrochloride, cytochrome C and tocopherol nicotinate; steroid drugs such as hydrocortisone, prednisolone, dexamethasone and betamethasone; wound therapeutic accelerators such as growth factors, heparin derivatives and collagen; as well as physiologically active polypeptide, hormone agents, anti-tuberculosis drugs, styptics, anti-diabetes therapeutic drugs, vasodilators, anti-arrhythmia drugs, cardiac drugs, anti-allergic drugs, anti-dipressant drugs, anti-epilepsy drugs, muscular relaxants, antitussive/expectorant drugs, antibiotics, etc.

Further, the polysaccharide pseudo-sponge of the present invention has such a property of preventing cells, etc., from being infiltrated thereinto, and therefore, can be suitably used as a base material of culture medium for cells or tissues.

EXAMPLES

The present invention is described in more detail below by Examples, but the Examples are only illustrative and not intended to limit the scope of the present invention. Meanwhile, the definitions of technical terms and measuring methods used in the Examples are as follows.

(1) Degree of Substitution of Photoreactive Group

The degree of substitution of a photoreactive group in the case where the photoreactive group is introduced into a carboxyl group of glycosaminoglycan as a polysaccharide, means a percentage of the number of photoreactive groups introduced per a repeating disaccharide unit. The amount of glycosaminoglycan required for calculation of the degree of substitution of a photoreactive group was measured by a carbazole method using a calibration curve thereof, and the amount of cinnamic acid when using cinnamic acid or a substituted cinnamic acid as a photoreactive substance was measured by an absorbance measuring method (measuring wavelength: 269 nm) using a calibration curve thereof.

(2) Crosslinking Ratio

The crosslinking ratio was determined as follows. That is, 1 g of a sample material to be measured was hydrolyzed with 1 mL of a 1 mol/L sodium hydroxide aqueous solution for 1 hour. Then, after acidifying the obtained solution, photoreactive group-derived substances (monomers, dimers, etc.) were extracted with ethyl acetate, and the resultant extract was analyzed by a high-pressure liquid chromatography (HPLC) to measure an amount of the dimers by the method using a calibration curve thereof. The crosslinking ratio was expressed by a percentage of moles of the photoreactive groups converted into dimers to moles of photoreactive groups introduced into the polysaccharide.

Production Example 1

Production of Photoreactive Hyaluronic Acid

A mixed solution containing 250 mL of water and 375 mL of dioxane was added under stirring to 500 g of a 1 wt % aqueous solution of sodium hyaluronate (comb-derived product, produced by Seikagaku Co., Ltd.; weight-average molecular weight: 900,000). The resultant mixed solution was successively mixed with a solution prepared by dissolving 860 mg of N-hydroxysuccinimide in 2 mL of water (0.6 equivalent/hyaluronic acid disaccharide unit (mol/mol)), a solution prepared by dissolving 717 mg of 1-ethyl-3-(3-dimethylaminopropyl)carbodiimide hydrochloride (EDCl/HCl) in 2 mL of water (0.3 equivalent/hyaluronic acid disaccharide unit (mol/mol)) and a solution prepared by dissolving 903 mg of aminopropyl cinnamate hydrochloride ($HCl \cdot H_2N(CH_2)_3OCO-CH=CH-Ph$, wherein Ph represents a phenyl group) in 2 mL of water (0.3 equivalent/hyaluronic acid disaccharide unit (mol/mol)) at room temperature, and stirred for 2.5 hours. Then, the resultant reaction solution was mixed with a solution prepared by dissolving 2.5 g of sodium hydrogencarbonate in 50 mL of water, followed by stirring for one day, and further mixed with 30 g of sodium chloride. 2 L of ethanol was added to the obtained reaction solution to precipitate a solid. The thus precipitated solid was washed with a mixed solvent composed of ethanol and water (weight ratio: 80:20) two times and then with ethanol two times, and dried at room temperature over night, thereby obtaining 5.24 g of a white solid (3-aminopropyl cinnamate-introduced hyaluronic acid: also referred to as "cinnamic acid-introduced hyaluronic acid"). It was confirmed that the degree of substitution of cinnamic acid per repeating hyaluronic acid disaccharide unit was 8.2%. Meanwhile, aminopropyl cinnamate-introduced alginic acid and aminopropyl cinnamate-introduced carboxymethyl cellulose were respectively produced by the same method as described above.

Production Example 2

Production of Crosslinked Hyaluronic Acid Gel (1) The cinnamic acid-introduced hyaluronic acid obtained in Production Example 1 was dissolved in water for injection to prepare a 4 wt % aqueous solution thereof. The resultant solution was poured into a mold made of a reinforced glass plate which had a mold cavity of 6 cm×2.5 cm×1 mm (in thickness), and then irradiated with ultraviolet rays using a 3 kW metal halide lamp under water-cooling for 15 min for each surface thereof, thereby obtaining a transparent sheet-shaped gel (water content: 96% by weight). It was confirmed that the crosslinking ratio of the obtained gel was 30%.

(2) The same procedure as defined in the above (1) was conducted except for using a cinnamic acid-introduced hyaluronic acid having 4.6% as a degree of substitution, produced by the same method as defined in Production Example 1, thereby obtaining a transparent sheet-shaped gel. It was confirmed that the crosslinking ratio of the obtained gel was 13.6%. Meanwhile, the light irradiation was conducted using a 3 kW high-pressure mercury lamp such that the total amount of light irradiated was 100 $J/cm^2$.

Production Example 3

Production of Crosslinked Hyaluronic Acid Sponge (1) The cinnamic acid-introduced hyaluronic acid obtained in Production Example 1 was dissolved in water for injection to prepare a 4 wt % aqueous solution thereof. The resultant solution was poured into a mold made of a reinforced glass plate which had a mold cavity of 6 cm×2.5 cm×1 mm (in thickness), and then frozen at −20° C. The resultant frozen product was irradiated with ultraviolet rays in an amount of 2,000 $mJ/cm^2$ using a 800 w high-pressure mercury lamp from both surfaces thereof, thereby obtaining an opaque white sheet-shaped sponge (water content: 96% by weight). It was confirmed that the crosslinking ratio of the obtained sponge was 33%.

(2) The same procedure as defined in the above (1) was conducted except for using a cinnamic acid-introduced hyaluronic acid having 4.6% as a degree of substitution, produced by the same method as defined in Production Example 1, thereby obtaining an opaque white sheet-shaped sponge. It was confirmed that the crosslinking ratio of the obtained sponge was 16.2%. Meanwhile, the light irradiation was conducted using a 800 W high-pressure mercury lamp such that the total amount of light irradiated was 4 $J/cm^2$.

Example 1

Production of Polysaccharide Pseudo-Sponge 1 of the Present Invention

As a filling container for a photoreactive polysaccharide solution, there was used a mold made of a reinforced glass plate which had a mold cavity of 6 cm in length×2.5 cm in width×1 mm in thickness. First, the cinnamic acid-introduced hyaluronic acid obtained in Production Example 1 was dissolved in water for injection to prepare a 4 wt % aqueous solution thereof. The resultant solution was poured into the above mold and then irradiated with ultraviolet rays in an amount of 50 $J/cm^2$ for each surface thereof using a 3 kW metal halide lamp under water-cooling such that the total amount of light irradiated was 100 $J/cm^2$, and thereafter frozen at −20° C. The resultant frozen product was irradiated with ultraviolet rays in an amount of 100 $mJ/cm^2$ using a 800 W high-pressure mercury lamp from both surfaces thereof, thereby obtaining a translucent sheet-shaped polysaccharide pseudo-sponge 1 of the present invention (water content: 96% by weight). It was confirmed that the crosslinking ratio of the obtained polysaccharide pseudo-sponge 1 was 33%.

Example 2

Production of Polysaccharide Pseudo-Sponge 2 of the Present Invention

The same procedure as defined in Example 1 was conducted except for using a cinnamic acid-introduced hyaluronic acid having 4.6% as a degree of substitution, produced by the same method as defined in Production Example 1, thereby obtaining a translucent sheet-shaped polysaccharide pseudo-sponge 2 of the present invention. It was confirmed that the crosslinking ratio of the obtained polysaccharide pseudo-sponge 2 was 17.0%. Meanwhile, the light irradiation after being frozen at −20° C. was conducted using a 800 W high-pressure mercury lamp such that the total amount of light irradiated was 1 J/cm$^2$.

<Breaking Strength Test>

The polysaccharide pseudo-sponge 1 of the present invention was tested by the method described in the present specification to measure a breaking strength thereof. In the test, there was used a texture analyzer "TA-XT2" (manufactured by Stable Micro Systems Co., Ltd.). Further, as control samples, the crosslinked hyaluronic acid gel produced in Production Example 2(1) and the crosslinked hyaluronic acid sponge produced in Production Example 3(1) were subjected to the same measurement as described above. The results of the measurement are shown in FIG. 1. As a result, it was confirmed that the polysaccharide pseudo-sponge 1 of the present invention had a breaking strength of about 420 g which was not less than 8 times that of the crosslinked hyaluronic acid gel and slightly less than 4 times that of the crosslinked hyaluronic acid sponge.

<Blue Dextran Dyeaffinity Test>

Figure 2:
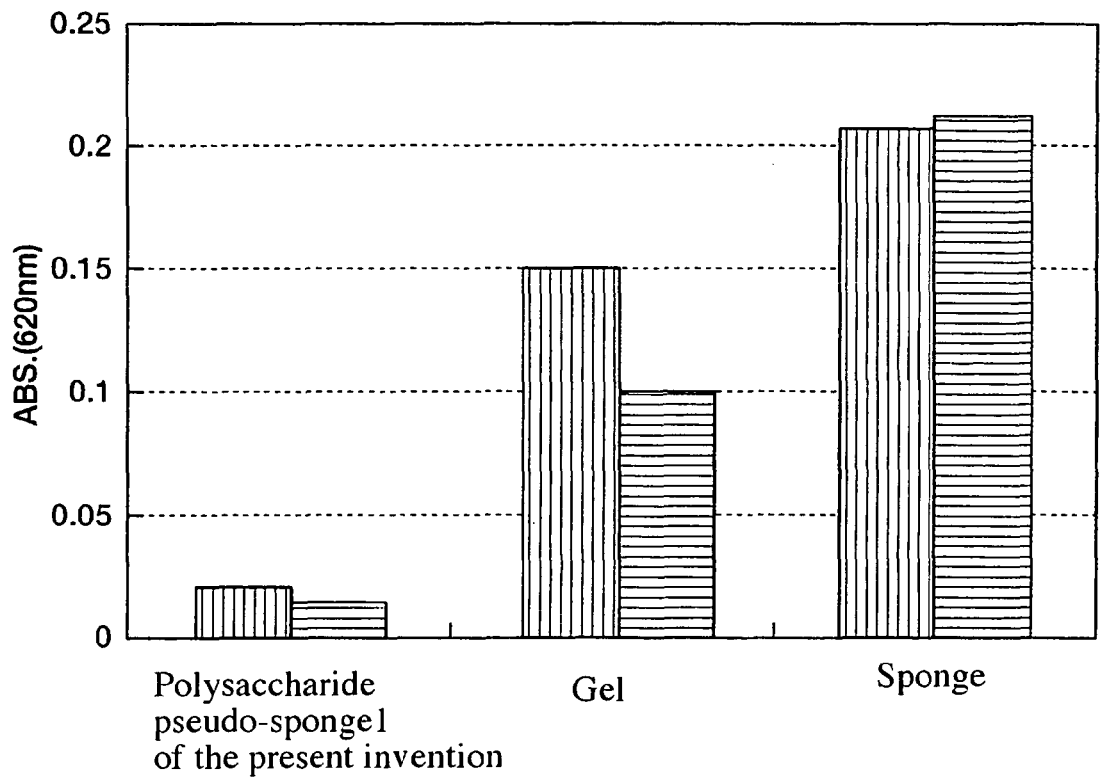
FIG. 2 is a graph showing a blue dextran dyeaffinity of the polysaccharide pseudo-sponge 1 of the present invention, in which a bar with a vertical stripe represents results obtained by a dipping method, whereas a bar with a horizontal stripe represents results obtained by a soaking method.

The polysaccharide pseudo-sponge 1 of the present invention was subjected to dyeing test by the method (dipping method and soaking method) described in the present specification. Further, as control samples, the crosslinked hyaluronic acid gel produced in Production Example 2(1) and the crosslinked hyaluronic acid sponge produced in Production Example 3(2) were subjected to the same measurement as described above. The results of the measurement are shown in FIG. 2. In FIG. 2, the bar with a vertical stripe represents results by a dipping method, whereas the bar with a horizontal stripe represents results by a soaking method. It was confirmed that the polysaccharide pseudo-sponge 1 of the present invention had such a dyeaffinity that an absorbance thereof was 0.02 which was about ½ time that of the crosslinked hyaluronic acid gel and about 1/10 time that of the crosslinked hyaluronic acid sponge. Meanwhile, it was considered that the unexpectedly high dyeaffinity of the gel was due to not penetration of blue dextran into the gel but absorption of blue dextran onto the surface of the gel.

<Swelling Test>

Figure 3:
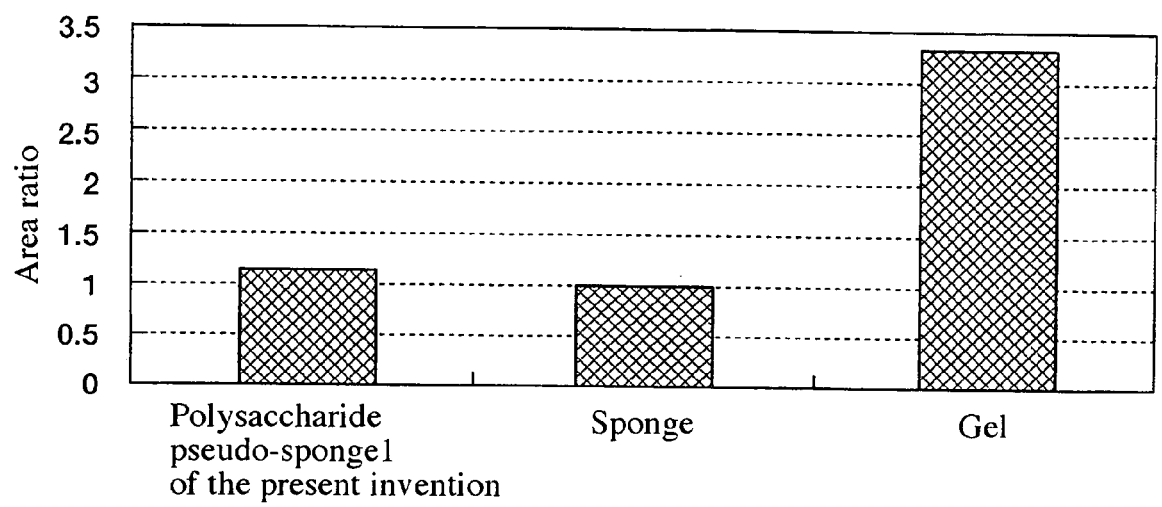
FIG. 3 is a graph showing a swelling property of the polysaccharide pseudo-sponge 1 of the present invention.

The polysaccharide pseudo-sponge 1 of the present invention was subjected to swelling test by the method described in the present specification. Further, as control samples, the crosslinked hyaluronic acid gel produced in Production Example 2(1) and the crosslinked hyaluronic acid sponge produced in Production Example 3(1) were subjected to the same measurement as described above. The results of the measurement are shown in FIG. 3. In FIG. 3, the area ratio means A2/A1 wherein A1 represents an area of the test specimen before immersing in water for injection, and A2 represents an area of the test specimen after immersing in water for injection. Meanwhile, the area of the test specimen means an area calculated from the length and width thereof. As a result, it was confirmed that the polysaccharide pseudo-sponge 1 of the present invention had a swelling ratio of about 20% (area ratio: 1.2), the crosslinked hyaluronic acid sponge underwent no swelling (swelling ratio: 0%; area ratio: 1.0), and the crosslinked hyaluronic acid gel had a swelling ratio of 240% (area ratio: 3.4).

<Enzymatic Degradation Ability Test>

Figure 4:
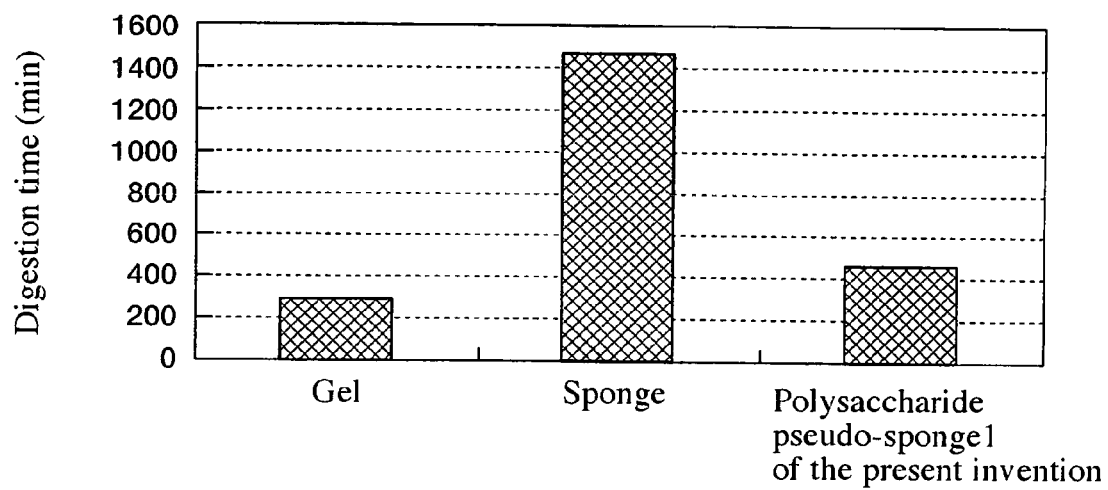
FIG. 4 is a graph showing an enzymatic degradation ability of the polysaccharide pseudo-sponge 1 of the present invention.

The polysaccharide pseudo-sponge 1 of the present invention was subjected to degradation ability test by the method described in the present specification. Further, as control samples, the crosslinked hyaluronic acid gel produced in Production Example 2(1) and the crosslinked hyaluronic acid sponge produced in Production Example 3(1) were subjected to the same measurement as described above. The results of the measurement are shown in FIG. 4. As a result, it was confirmed that the polysaccharide pseudo-sponge 1 of the present invention exhibited a degradation time of about 500 min which was 1.6 times that of the crosslinked hyaluronic acid gel. On the other hand, the crosslinked hyaluronic acid sponge required a degradation time 4.8 times that of crosslinked hyaluronic acid gel. Due to this fact, it was confirmed that the polysaccharide pseudo-sponge 1 of the present invention had an adequate enzymatic degradation ability.

Example 3

Production of Polysaccharide Pseudo-Sponge 3 of the Present Invention

The cinnamic acid-introduced hyaluronic acid having 8.2% as a degree of substitution, produced by the same method as defined in Production Example 1 was dissolved in water for injection to prepare a 4 wt % aqueous solution thereof. Next, the resultant solution was poured into the same container as used in Example 1 and then irradiated with ultraviolet rays in an amount of 50 J/cm$^2$ for each surface thereof using a 3 kW metal halide lamp under water-cooling such that the total amount of light irradiated was 100 J/cm$^2$, and thereafter frozen at −20° C. The resultant frozen product was taken out of the container, and freeze-dried at room temperature. The thus obtained freeze-dried product was irradiated with ultraviolet rays using a 800 W high-pressure mercury lamp from both surfaces thereof such that the total amount of light irradiated was 5 J/cm$^2$, thereby obtaining a polysaccharide pseudo-sponge 3. It was confirmed that the crosslinking ratio of the obtained polysaccharide pseudo-sponge 3 was 21.5%.

Various properties of the polysaccharide pseudo-sponge 3 were measured by the same methods as used for the polysaccharide pseudo-sponge 1. As a result, it was confirmed that the polysaccharide pseudo-sponge 3 exhibited a breaking strength of 229.4 g, an absorbance of 0.021 as measured by dyeaffinity test using a dipping method and a soaking method, and a swelling ratio of 50%.

<Study on Sustained Drug-Releasability of Polysaccharide Pseudo-Sponge of the Present Invention>

The cinnamic acid-introduced hyaluronic acid having 8.2% as a degree of substitution, produced by the same method as defined in Production Example 1 was dissolved in water for injection to prepare a 4 wt % aqueous solution thereof. Then, blue dextran having a molecular weight of 2,000,000 as a model substance for drugs was added to the thus obtained solution such that the concentration of blue dextran in the solution was 10 mg/mL, and intimately mixed with each other. The resultant solution was poured into a mold having a mold cavity of 5.5 cm in length×3.5 cm in width×0.5 mm in thickness, and then irradiated with ultraviolet rays in an amount of 50 J/cm$^2$ for each surface thereof using a 3 kW metal halide lamp under water-cooling such that the total amount of light irradiated was 100 J/cm$^2$, and thereafter frozen at −20° C. The resultant frozen product was irradiated with ultraviolet rays while being kept in a frozen state using a 800 W high-pressure mercury lamp from both surfaces thereof such that the total amount of light irradiated was 500 mJ/cm$^2$, thereby obtaining a blue dextran-containing polysaccharide pseudo-sponge (hereinafter occasionally referred to as "BD-containing polysaccharide pseudo-sponge"). It was confirmed that the crosslinking ratio of the obtained BD-containing polysaccharide pseudo-sponge was 20%. Five sheets of the BD-containing polysaccharide pseudo-sponge were prepared.

Using four rats, a sheet of the thus obtained BD-containing polysaccharide pseudo-sponge was placed within a middle-incised abdominal cavity of each rat, and the respective sheets of the BD-containing polysaccharide pseudo-sponge were recovered from an inside of the abdominal cavity after passage of each of one week, two weeks, three weeks and four weeks to measure a residual amount of blue dextran in the BD-containing polysaccharide pseudo-sponge as well as a residual amount of the polysaccharide pseudo-sponge itself therein.

The measurement of residual amount of the blue dextran was conducted by measuring a 620 nm absorbance of a solution prepared by hydrolyzing the recovered BD-containing polysaccharide pseudo-sponge with 50 mL of a 1N NaOH solution at room temperature for 1 hour, using a spectrophotometer. The residual amount of the blue dextran at each recovery time was determined as a ratio based on an amount (100) of blue dextran contained in the BD-containing polysaccharide pseudo-sponge before being placed within the abdominal cavity.

The residual amount of the polysaccharide pseudo-sponge was measured by quantitative determination of an uronic acid content in the solution used above for measuring the residual amount of the blue dextran using carbazole method. The residual amount of the polysaccharide pseudo-sponge at each recovery time was determined as a ratio of the thus measured uronic acid content to an uronic acid content (100) in the BD-containing polysaccharide pseudo-sponge before being placed within the abdominal cavity.

Figure 5:
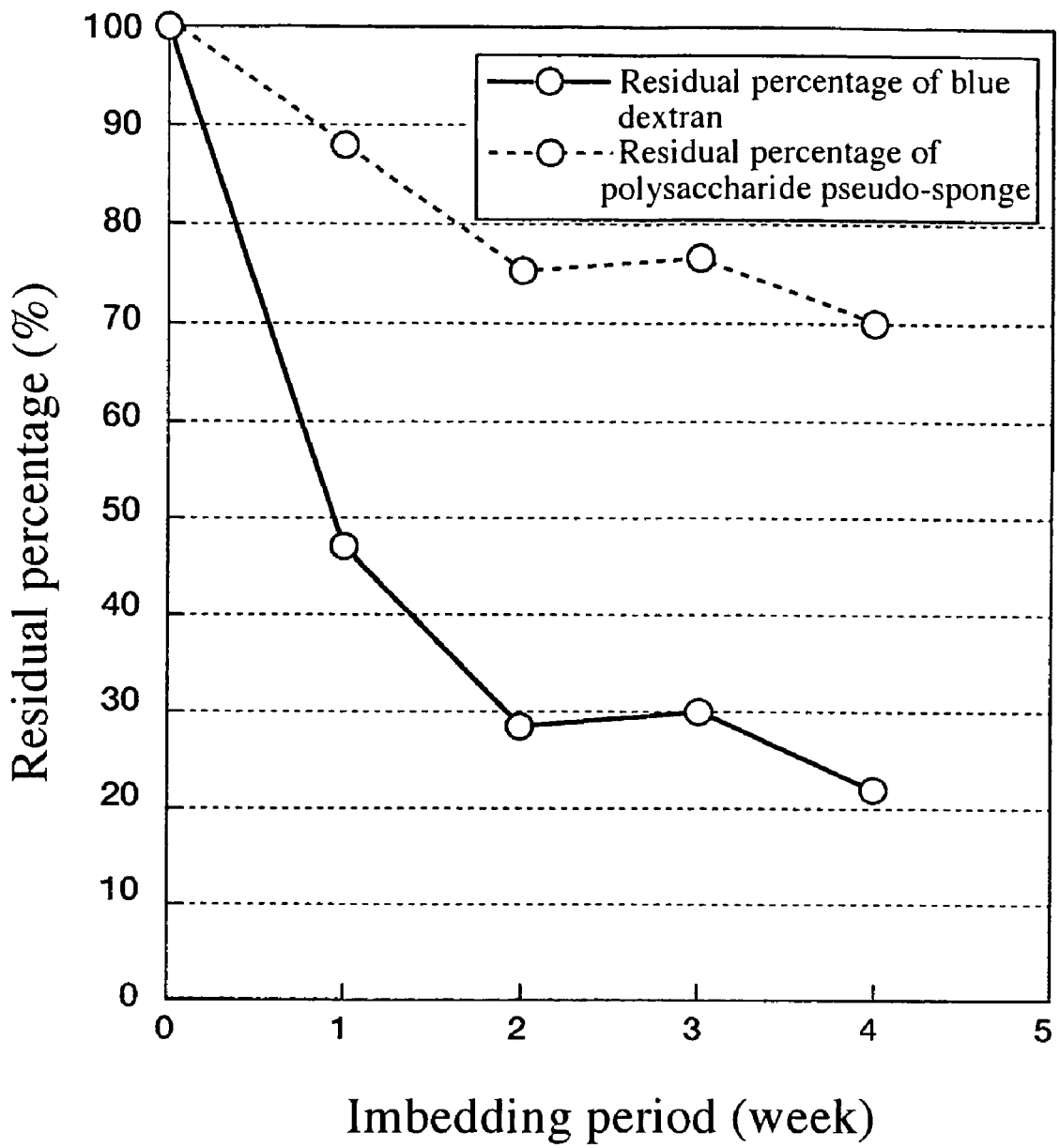
FIG. 5 is a graph showing percentages of residual blue dextran and residual polysaccharide pseudo-sponge as measured for a period, in which a blue dextran-containing polysaccharide pseudo-sponge is embedded in an abdominal cavity of a rat.

The results of measurements of residual percentages of the blue dextran and polysaccharide pseudo-sponge with respect to each imbedding period of the sponge within the abdominal cavity of rats, are shown in FIG. 5.

From the results shown in FIG. 5, it was confirmed that even after passage of 4 weeks from the placement of the sponge within the abdominal cavity, the residual percentage of the blue dextran was about 22% and the residual percentage of the polysaccharide pseudo-sponge was 70%. Although release of the blue dextran which was considered to be due to burst of the sponge, was recognized after one week from dosage of the sponge, since the residual amount of the blue dextran was subsequently decreased with reduction in residual amount of the polysaccharide pseudo-sponge, it was suggested that the blue dextran was released along with degradation of the polysaccharide pseudo-sponge. As a result, it was confirmed that the polysaccharide pseudo-sponge in which a drug is simply mixed could continuously release the drug over a period of one month or longer without causing any chemical bond therebetween. Therefore, it is considered that the polysaccharide pseudo-sponge of the present invention can be suitably used as a base material for sustained release of drugs.

<Observation Using Scanning Electron Microscope>

The polysaccharide pseudo-sponge 2 of the present invention was observed by a scanning electron microscope. Upon the observation by a scanning electron microscope, there was used a freeze-dried product of the polysaccharide pseudo-sponge 2. FIG. 6 shows an enlarged view (photograph as substitute for drawing) of the surface of the polysaccharide pseudo-sponge 2 of the present invention, and FIG. 7 shows an enlarged view (photograph as substitute for drawing) of the section of the polysaccharide pseudo-sponge 2 of the present invention. Also, the crosslinked hyaluronic acid gel produced in Production Example 2(2) and the crosslinked hyaluronic acid sponge produced in Production Example 3(2) were similarly subjected to the observation by a scanning electron microscope. FIG. 8 shows an enlarged view (photograph as substitute for drawing) of the surface of the crosslinked hyaluronic acid gel produced in Production Example 2(2); FIG. 9 shows an enlarged view (photograph as substitute for drawing) of the section of the crosslinked hyaluronic acid gel produced in Production Example 2(2); FIG. 10 shows an enlarged view (photograph as substitute for drawing) of the surface of the crosslinked hyaluronic acid sponge produced in Production Example 3(2); and FIG. 11 shows an enlarged view (photograph as substitute for drawing) of the section of the crosslinked hyaluronic acid sponge produced in Production Example 3(2).

From the results of the observation by a scanning electron microscope, the reason why the polysaccharide pseudo-sponge of the present invention exhibits a high strength is suggested as follows. That is, the polysaccharide pseudo-sponge has a steric structure constituted from planes, whereas the sponge has a structure constituted from "columns (lines)". Since the pseudo-sponge and the sponge have substantially no difference in pore size therebetween, it is readily suggested that the strength of the pseudo-sponge constituted from planes is higher than that of the sponge constituted from lines. In addition, the polysaccharide pseudo-sponge has a considerably uniform wall surface. The smooth surface is usually improved in strength as compared to a rough surface. Further, the polysaccharide pseudo-sponge is constituted from a continuity of bags like closed cells, whereas the sponge has a structure composed of interconnected pores, and the gel is barred but has a bag structure.

It is considered that the above difference in structure between the polysaccharide pseudo-sponge and the sponge and gel reflects the difference in blue dextran dyeaffinity therebetween. That is, the pseudo-sponge has a smooth surface as if the surface thereof is covered with a thin film, so that the blue dextran solution is readily flowed thereover, resulting in low dyeaffinity thereof. On the other hand, the reason why the gel exhibited a certain dyeaffinity notwithstanding the gel is usually known as a substance through which blue dextran particles having a weight-average molecular weight of 2,000,000 cannot be penetrated, is considered to be that the blue dextran particles were adsorbed on the rough surface of the gel.

Further, the swelling property of the gel is considered as follows. That is, since a wall surface of the gel is of a pleated shape, it is suggested that the gel has a high-order folded structure. Therefore, it is considered that the gel exhibits a swelling property due to strain within the high-order structure as well as margin in the expanding direction thereof.

Example 4

Production of Polysaccharide Pseudo-Sponge of the Present Invention Using Cinnamic Acid-Introduced Alginic Acid One gram of photoreactive alginic acid obtained by introducing aminopropyl cinnamate into 4% of whole carboxyl groups of sodium alginate (produced by Wako Junyaku Kogyo Co., Ltd.) was dissolved in 25 mL of water for injection to prepare a 4 wt % photoreactive alginic acid aqueous solution. 1 mL of the resultant aqueous solution was filled and sealed in a high-density polypropylene pack such that a thickness of the aqueous solution filled in the pack was 1 mm, irradiated with light in an amount of 2,500 mJ/cm$^2$ using a 800 W high-pressure mercury lamp, and then frozen in a dry ice/ethanol bath at −40° C. Next, the resultant frozen product was further irradiated with light in an amount of 250 mJ/cm$^2$ using a high-pressure mercury lamp while being kept in a frozen state, thereby obtaining a crosslinked alginic acid pseudo-sponge.

Example 5

Production of Polysaccharide Pseudo-Sponge of the Present Invention Using Cinnamic Acid-Introduced Carboxymethyl Cellulose One gram of photoreactive carboxymethyl cellulose obtained by introducing aminopropyl cinnamate into about 10% of whole carboxyl groups of sodium carboxymethyl cellulose (produced by Nakari-Tesc Co., Ltd.) was dissolved in 25 mL of water for injection to prepare a 4 wt % photoreactive carboxymethyl cellulose aqueous solution. 1 mL of the resultant aqueous solution was filled and sealed in a high-density polypropylene pack such that a thickness of the aqueous solution filled in the pack was 1 mm, irradiated with light in an amount of 2,500 mJ/cm$^2$ using a 800 W high-pressure mercury lamp, and then frozen in a dry ice/ethanol bath at −40° C. Next, the resultant frozen product was further irradiated with light in an amount of 250 mJ/cm$^2$ using a high-pressure mercury lamp while being kept in a frozen state, thereby obtaining a crosslinked carboxymethyl cellulose pseudo-sponge.

The invention claimed is:

1. A polysaccharide pseudo-sponge produced by a crosslinking reaction of a photoreactive polysaccharide obtained by introducing a photoreactive group into a polysaccharide, said polysaccharide pseudo-sponge exhibiting a low swelling property and an enzymatic degradation time which satisfy the following properties (I) and (II), respectively:
   (I) a swelling ratio of not more than 125% as calculated from the values measured by immersing a test specimen having a thickness of 1 mm, a length of 10 mm and a width of 10 mm, and a solvent content of 96% by weight, in water for injection at room temperature for 1 hour, according to the following formula:

Swelling ratio=$\{(S2-S1)/S1\} \times 100$ wherein S1 represents an area of the test specimen before the immersion, and S2 is an area of the test specimen after the immersion, in which the area is calculated from the length and width of the test specimen; and
   (II) an enzymatic degradation time of the polysaccharide pseudo-sponge is not more than 1300 minute as measured by subjecting a test specimen having a thickness of 1 mm, a length of 20 mm and a width of 10 mm, and a solvent content of 96% by weight, to a polysaccharide degrading enzyme in a reaction mixture containing 1 mL of a 5 mmol/L phosphate buffered saline, 0.2 mL of a 1 mmol/L acetate buffer solution and 0.2 mL of a 5TRU (Turbidity Reducing Unit)/mL the enzyme solution at 50° C.

2. The polysaccharide pseudo-sponge according to claim 1, wherein the light irradiated has a wavelength of 180 to 650 nm.

3. The polysaccharide pseudo-sponge according to claim 1, wherein a crosslinking ratio of the polysaccharide pseudo-sponge is not less than 1%.

4. The polysaccharide pseudo-sponge according to claim 1, wherein a breaking strength of the polysaccharide pseudo-sponge is not less than 200 g as measured by piercing and breaking a test specimen having a thickness of 1 mm, a length of 60 mm and a width of 25 mm, and a solvent content of 96% by weight, with a 12.7 mm-diameter spherical probe at 24° C. and a piercing speed of 1 mm/s by using a texture analyzer.

5. The polysaccharide pseudo-sponge according to claim 1, wherein the polysaccharide is homoglycan, heteroglycan or a derivative thereof.

6. The polysaccharide pseudo-sponge according to claim 5, wherein the homoglycan is glucan.

7. The polysaccharide pseudo-sponge according to claim 5, wherein the heteroglycan is glycosaminoglycan.

8. The polysaccharide pseudo-sponge according to claim 7, wherein the glycosaminoglycan is hyaluronic acid.

9. The polysaccharide pseudo-sponge according to claim 1, wherein the photoreactive group is a residue of a compound formed by ester-bonding or amide bonding amino alcohol to a carboxyl group of cinnamic acid.

10. A medical material comprising the polysaccharide pseudo-sponge as defined in claim 1.

11. The medical material according to claim 10, which is used as an antiadhesive material.

12. The medical material according to claim 10, which is used as a base material for sustained release of drug.

13. A polysaccharide pseudo-sponge produced by irradiating light to a solution of a photoreactive polysaccharide obtained by introducing a photoreactive group into a polysaccharide to obtain a polysaccharide gel having a shape-retention property, freezing or freeze-drying the obtained polysaccharide gel, and then irradiating light to the resultant frozen or freeze-dried polysaccharide gel,
   said polysaccharide pseudo-sponge exhibiting a low swelling property and an enzymatic degradation time which satisfy the following properties (I) and (II), respectively:
   (I) a swelling ratio of not more than 125% as calculated from the values measured by immersing a test specimen having a thickness of 1 mm, a length of 10 mm and a width of 10 mm, and a solvent content of 96% by weight, in water for injection at room temperature for 1 hour, according to the following formula:

Swelling ratio=$\{(S2-S1)/S1\} \times 100$ wherein S1 represents an area of the test specimen before the immersion, and S2 is an area of the test specimen after the immersion, in which the area is calculated from the length and width of the test specimen; and
   (II) an enzymatic degradation time of the polysaccharide pseudo-sponge is not more than 1300 minute as measured by subjecting a test specimen having a thickness of 1 mm, a length of 20 mm and a width of 10 mm, and a solvent content of 96% by weight, to a polysaccharide degrading enzyme in a reaction mixture containing 1 mL of a 5 mmol/L phosphate buffered saline, 0.2 mL of a 1 mol/L acetate buffer solution and 0.2 mL of a 5TRU (Turbidity Reducing Unit)/mL the enzyme solution at 50° C.

14. The polysaccharide pseudo-sponge according to claim 13, wherein the solution of the photoreactive polysaccharide obtained by introducing a photoreactive group into a polysaccharide, further comprises an aqueous solvent-miscible substance selected from the group consisting of alcohols, surfactants and chelating agents.

15. A polysaccharide pseudo-sponge according to claim 13, wherein the polysaccharide is hyaluronic acid and the photoreactive group is a cinnamic acid derivative.

* * * * *